(12) United States Patent
Lopez et al.

(10) Patent No.: US 8,658,734 B2
(45) Date of Patent: Feb. 25, 2014

(54) SYNTHESIS OF STABLE ELASTOMERIC NEGATIVE ACOUSTIC CONTRAST PARTICLES

(75) Inventors: Gabriel Lopez, Durham, NC (US); Nick Carroll, Albuquerque, NM (US); Kevin Cushing, Albuquerque, NM (US); Dimiter N Petsev, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 151 days.

(21) Appl. No.: 13/320,454

(22) PCT Filed: May 11, 2010

(86) PCT No.: PCT/US2010/034411
§ 371 (c)(1),
(2), (4) Date: Nov. 14, 2011

(87) PCT Pub. No.: WO2010/132471
PCT Pub. Date: Nov. 18, 2010

(65) Prior Publication Data
US 2012/0065329 A1    Mar. 15, 2012

Related U.S. Application Data

(60) Provisional application No. 61/216,024, filed on May 11, 2009, provisional application No. 61/227,962, filed on Jul. 23, 2009.

(51) Int. Cl.
*C08L 83/04*    (2006.01)
(52) U.S. Cl.
USPC .......................................................... 524/860

(58) Field of Classification Search
USPC .......................................................... 524/860
See application file for complete search history.

(56) References Cited

U.S. PATENT DOCUMENTS

| | | | |
|---|---|---|---|
| 5,147,631 | A | 9/1992 | Glajch et al. |
| 5,487,390 | A | 1/1996 | Cohen et al. |
| 7,340,957 | B2 | 3/2008 | Kaduchak et al. |
| 2006/0102871 | A1 | 5/2006 | Wang et al. |
| 2008/0245709 | A1 | 10/2008 | Kaduchak et al. |

FOREIGN PATENT DOCUMENTS

| | | |
|---|---|---|
| WO | 9415654 A1 | 7/1994 |
| WO | 2006031299 A2 | 3/2006 |
| WO | 2008122051 A1 | 10/2008 |

*Primary Examiner* — Edward Cain
(74) *Attorney, Agent, or Firm* — Gonzales Patent Services; Ellen M Gonzales

(57) ABSTRACT

We describe methods for synthesis and formulations of stable elastomeric negative acoustic contrast particles with controllable compressibility and density. These elastomeric negative acoustic contrast particles have a density/compressibility ratio that is less than that of water and therefore exhibit negative acoustic contrast under acoustic radiation exposure. This negative acoustic contrast allows our elastomeric negative acoustic contrast particles to be acoustically manipulated (e.g. separated) differently from other components (e.g. cells) within an aqueous solution. This disclosure also describes methods for biofunctionalization of the elastomeric negative acoustic contrast particles and as an example their use as platforms for bioassays. Potential applications of these elastomeric negative acoustic contrast particles include sensitive bioassays based on acoustic flow cytometry and other types of techniques that utilize acoustic fields, including ultrasound imaging and ultrasound triggered drug delivery.

13 Claims, 8 Drawing Sheets

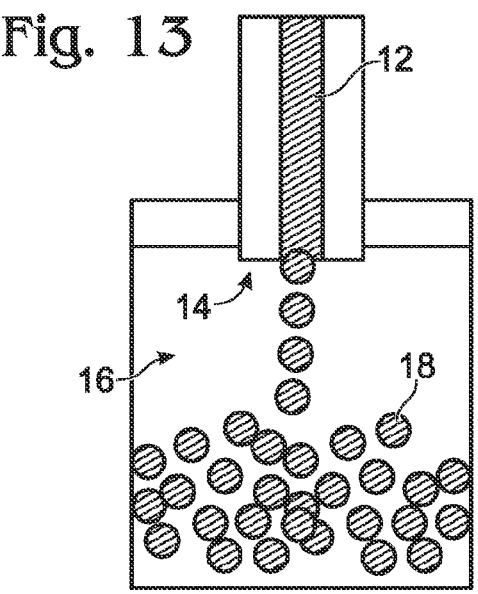
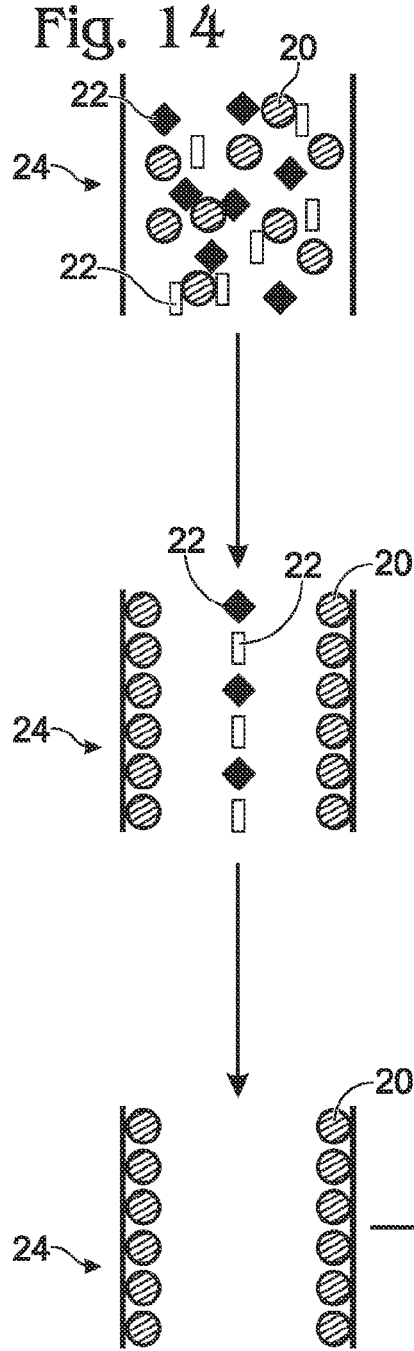

Fig. 15
Fig. 16
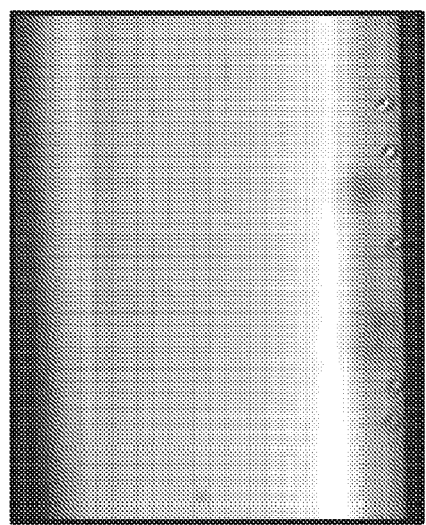
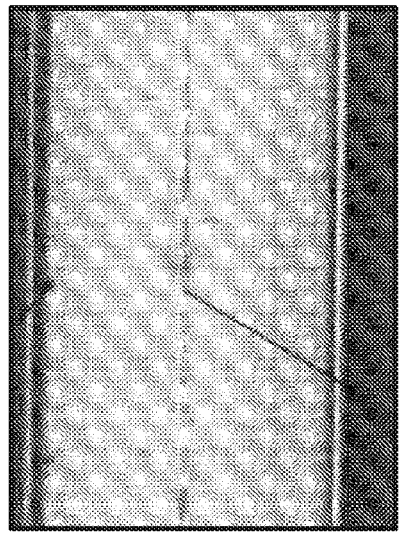
Fig. 17
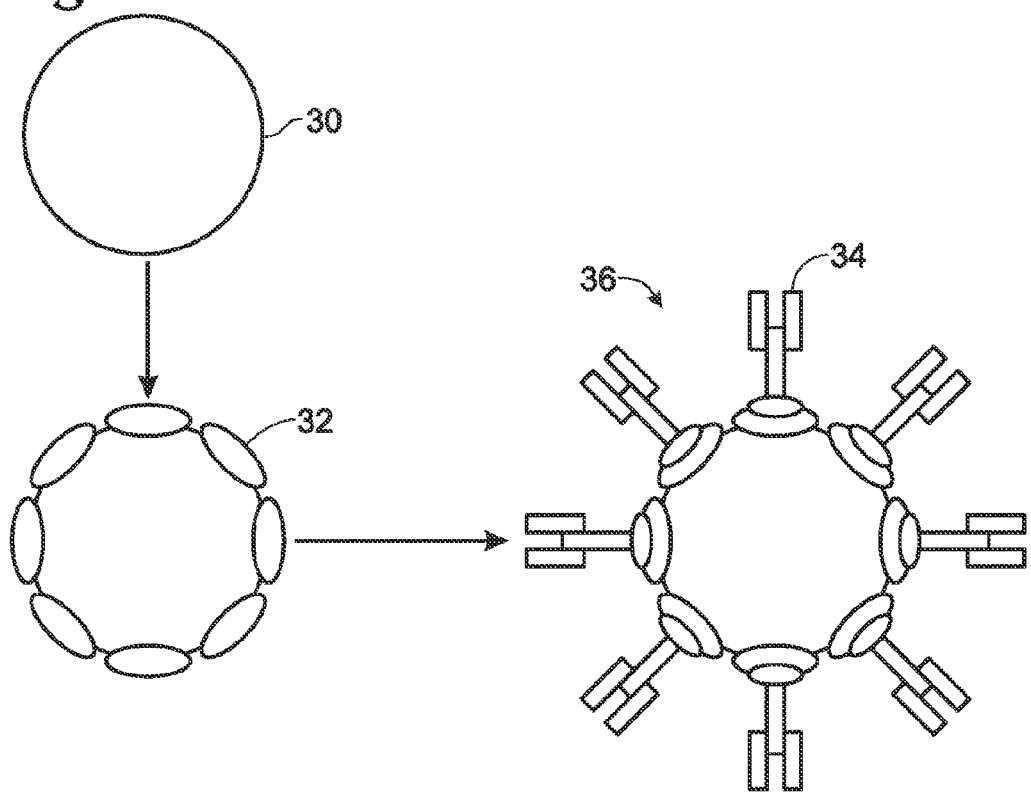

US 8,658,734 B2

SYNTHESIS OF STABLE ELASTOMERIC NEGATIVE ACOUSTIC CONTRAST PARTICLES

CROSS-REFERENCE TO RELATED APPLICATIONS

This application claims the benefit of U.S. Provisional Patent Application Ser. No. 61/216,024, filed May 11, 2009 and U.S. Provisional Patent Application Ser. No. 61/227,962, filed Jul. 23, 2009, each of which is hereby incorporated by reference in its entirety.

FIELD OF THE INVENTION

This invention relates generally to stable elastomeric negative acoustic contrast particles and, specifically, to the synthesis of stable elastomeric negative acoustic contrast particles with predetermined mechanical properties (e.g. density/compressibility ratio).

BACKGROUND OF THE INVENTION

Particles within an acoustic focusing chamber (or acoustic flow cytometer) can be separated from other components in a solution using acoustic force manipulation. See e.g., U.S. Pat. No. 7,340,957 issued Mar. 11, 2008, which is incorporated by reference. Particles exposed to an ultrasonic standing wave field will experience an average drift force positioning them at local pressure potential minima within an acoustic radiation pressure force potential. See e.g., US Patent Application Publication No. 2008/0245709, published Oct. 9, 2008, which is hereby incorporated by reference. The ability of ultrasonic radiation to separate particles derives from the particles' density/compressibility ratio. The density/compressibility contrast between particles and their host medium will determine the positioning of the particles under acoustic radiation exposure. Positive acoustic contrast particles that have a density/compressibility ratio greater than the surrounding medium will be positioned at local pressure potential minima nodes along the center of the focusing chamber (focused). Conversely, negative acoustic contrast particles with a smaller density/compressibility ratio than the surrounding medium will be positioned at local pressure potential minima antinodes along the side of the focusing chamber. After this positioning, positive acoustic contrast particles can be removed from the acoustic focusing chamber, leaving behind only negative acoustic contrast particles which can subsequently be focused to the center of the chamber for analysis.

Elastomers are long chained polymers that can be crosslinked to form elastic rubber. As a result of this crosslinked arrangement, elastomers distribute applied forces equally throughout the entire structure. This intrinsic attribute allows crosslinked elastomers to be compressed with an applied force or stress and recoil back to their original configuration without degradation occurring. This intrinsic mechanical property allows elastomeric particles to be used in applications requiring particle separations, concentrations, or manipulations using acoustic radiation pressure fields.

As described in the '709 patent application publication, most biological particles in aqueous solutions appear to exhibit positive acoustic contrast. Acoustic force manipulation has been used in the past to concentrate (focus) Chinese hamster cells, red blood cells, bacteria, fungal spores, and other types of biological particles in aqueous solution. See the '709 publication as well as Goddard, et al., Analytical Performance of an Ultrasonic Particle Focusing Flow Cytometer; Anal. Chem. (79), 8740-8746 (2007). Exploiting this property, acoustic radiation can be used to trap elastomeric negative acoustic contrast particles or separate them from many biological components within aqueous or unmodified biological samples. The '709 publication provides several examples of how this property, when combined with acoustic flow cytometry, can result in a powerful bioanalytical methodology.

SUMMARY

The present disclosure provides various novel methods for synthesizing elastomeric negative acoustic contrast particles. In general, a water-insoluble elastomer and a cross-linking agent are subjected to oil-in-water emulsion conditions suitable for droplet formation. The droplets are then cured to form stable elastomeric negative acoustic contrast particles. According to a first embodiment, elastomeric negative acoustic contrast particles are synthesized using a bulk (shaking or emulsified with a homogenizer) oil-in-water emulsion system. According to a second embodiment, elastomeric negative acoustic contrast particles are synthesized with the aid of microfluidic channels. According to a third embodiment, elastomeric negative acoustic contrast particles are synthesized using ink jet printing technology.

Synthesis of elastomeric negative acoustic contrast particles with predetermined density/compressibilities ratios, allows for the particles to be useful for a variety of applications involving acoustic radiation (e.g. particle separations, concentrations, and manipulations). The elastomeric negative acoustic contrast particles described herein, and the methods for preparing them, allow for control of compressibility and density, an essential feature to design negative acoustic contrast particles for acoustic-force based technologies. The ability to control the elastomeric negative acoustic contrast particles' density/compressibility ratio will allow them to be tailor-made for use as additives in paints, cosmetics (e.g. lotions, makeup) and other hygenic products (e.g. shampoos). The synthesis of elastomeric negative acoustic contrast particles with predetermined density/compressibility ratios, may also allow them to function as acoustic imaging agents that enhance image delineation during medical ultrasonography.

BRIEF DESCRIPTION OF THE DRAWINGS

FIG. 1 shows the results of emulsifying PDMS with 420 cST viscosity with 10% volume cross-linking agent.

FIG. 2 shows the results of emulsifying PDMS with 420 cST viscosity with 30% volume cross-linking agent.

FIG. 3 shows the results of emulsifying PDMS with 420 cST viscosity with 50% volume cross-linking agent.

FIG. 4 shows the results of emulsifying PDMS with 420 cST viscosity with 75% volume cross-linking agent.

FIG. 5 is a bright field image showing elastomeric negative acoustic contrast particles formed using an oil-in-water synthesis method.

FIG. 6 is a size distribution histogram of a population of elastomeric negative acoustic contrast particles formed using an oil-in-water synthesis method.

FIG. 7 shows decreased size distribution of elastomeric negative acoustic contrast particles (Sylgard 184) using an Isopore™ membrane filter (5 µm Pore Size).

FIG. 8 is a T-junction microfluidic device suitable for use with the methods described herein.

FIG. 9 is a bright field image showing elastomeric negative acoustic contrast particles formed using the T-junction microfluidic device of FIG. 4.

FIG. 13 depicts an embodiment of an ink-jet printing method for forming elastomeric negative acoustic contrast particles.

FIG. 14 is a diagram showing acoustic particle manipulation inside an acoustic flow chamber or inside an acoustic flow cytometer.

FIG. 15 is an image showing the effects of an acoustic radiation field on the elastomeric negative acoustic contrast particles of the present disclosure.

FIG. 16 is an image showing the effects of an acoustic radiation field on polystyrene positive acoustic contrast particles.

FIG. 17 shows a method of biofunctionalizing the elastomeric negative contrast acoustic particles described herein.

FIG. 22 shows the elastomeric negative acoustic contrast particles of FIG. 21 with the acoustic radiation field turned on.

DETAILED DESCRIPTION

Figure 1:
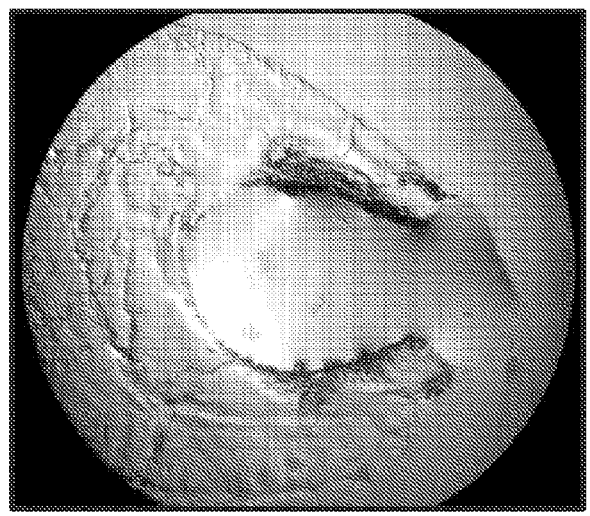

In this disclosure we describe versatile new methods for making stable elastomeric negative acoustic contrast particles whose density and compressibility can be well controlled. The elastomeric negative acoustic contrast particles described herein, as well as the synthetic methods for making and modifying them, allow for control of compressibility and density. Prior to droplet formation, the compressibility and density of elastomeric negative acoustic contrast particles can be pre-determined based on the concentration of crosslinking agent mixed into the water insoluble elastomer. According to some embodiments, the elastomeric particles have a density/compressibility ratio that is less than that of water and therefore exhibit negative acoustic contrast under acoustic radiation exposure. This property allows elastomeric particles to be designed to exhibit negative acoustic contrast when exposed to acoustic radiation. Accordingly, the present disclosure provides specific formulations for elastomeric particles that exhibit negative acoustic contrast. An important feature of the methods described herein is that they allow for easy incorporation of molecular, or other markers, into the elastomeric negative acoustic contrast particles that can be used to "barcode" the identity of that particle. This feature is especially important in multiplexed assays in which different particles within a given population have specificity for different analytes. See, e.g., Nolen, et al., Multiplexed and Micro-particle based Analysis Quantitative Tools for the Large Scale Analysis of Biological Systems; Cytometry A, Vol. 69, No. 5 (2006).

According to a first embodiment, polydisperse (poly-sized) populations of stable elastomeric negative acoustic contrast particles can be formed using an oil-in-water emulsion system. In this system, the water-insoluble elastomer-of-choice, along with a crosslinking agent, is poured into an aqueous solution containing a stabilizing surfactant. Suitable elastomers that could be used to produce elastomeric negative acoustic contrast particles include, but not limited to, natural rubbers, polyurethanes, silicone rubbers, butyl rubbers, polybutadienes, styrene butadienes, fluoroelastomers, polyether block amides, ethylene-vinyl acetates, and polyacrylic rubber. For certain elastomers, it may be useful to use a different type of emulsion (e.g., water in oil, oil in fluorocarbon, fluorocarbon in oil, water in fluorocarbon, fluorocarbon in water, or microemulsions). The mixture is then emulsified by shaking or mixing with enough force as to shear the oil (water insoluble elastomer) component into individual polydisperse droplets. The size of the droplets is dependent upon the amount of energy applied and the duration of the mixing process. Once droplets have been formed with this method, they can be crosslinked, by curing with heat, UV light, pressure, gamma radiation, electron beam, or other types of radiation exposure for a specified period of time, to form stable polydisperse elastomeric negative acoustic contrast particles.

According to an embodiment, the elastomeric negative acoustic contrast particles of the present disclosure are specifically engineered with predetermined density/compressibility ratios. Selection of the density/compressibility ratio allows for the control of the particles' behavior within an acoustic field. The primary acoustic force on particles in an acoustic standing wave field can be calculated from the following primary acoustic force ($F_p$) equation; Chem. Soc. Rev., 2007, 36, 492-506:

$$F_p = -\left(\frac{\pi p^2 V_p \beta_o}{2\lambda}\right) \varphi(\beta, \rho) \sin(2kx) \quad \text{Equation 1}$$

$$\varphi(\beta, \rho) = \frac{5\rho_p - 2\rho_o}{2\rho_p + \rho_o} - \frac{\beta_p}{\beta_o} \quad \text{Equation 2}$$

$V_p$ = volume of the particle
$p$ = acoustic pressure amplitude
$\beta_o$ = compressibility of the surrounding medium
$\beta_p$ = compressibility of the particle
$\rho_p$ = density of the particle
$\rho_o$ = density of the surrounding medium
$k$ = wave number $\left(\frac{2\pi}{\lambda}\right)$
$x$ = distance from a pressure node
$\varphi(\beta, \rho)$ = acoustic contrast factor.
  determines the direction of the acoustic force Equations (1 and 2) explain the magnitude and the direction of the acoustic force exerted on particles within an acoustic standing wave field. The value (+ or −) of $\phi(\beta, \rho)$, which is based on compressibility and density differences between particles and their host medium, will determine the direction of the acoustic force exerted on the particles. If $\phi(\beta, \rho)$ has a positive (+) value then the acoustic field will exert a time-averaged drift force moving the particles to acoustic pressure nodes. For the purposes of the present disclosure, particles exhibiting this type of behavior within an acoustic field are referred to as positive acoustic contrast particles. However, if φ(β, ρ) has a negative (−) value then the acoustic field will exert a time-averaged drift force moving the particles to acoustic pressure antinodes. For the purposes of the present disclosure, particles exhibiting this type of behavior within an acoustic filed are referred to as negative acoustic contrast particles. Generally, if a particle is less dense and more compressible than its aqueous media, it will have a negative value for φ(β, ρ), therefore functioning as a negative acoustic contrast particle under an acoustic standing wave field. On the other hand, if a particle is denser and less compressible than its aqueous media, it will have a positive value for φ(β, ρ), therefore functioning as a positive acoustic contrast particle under an acoustic standing wave field. It will be appreciated that the methods described herein can be used to form both negative and positive acoustic contrast particles.

According to the primary force equation ($F_p$) the magnitude of the acoustic force exerted on particles, in an acoustic standing wave field, is related to φ(β, ρ). As a result of this, the compressibility and density of the particles can be tuned to affect their behavior under acoustic standing wave fields. This tuning can be pre-determined, prior to particle formation, by the amount of crosslinking agent added to the water insoluble elastomer. Specifically, the more crosslinking agent added, the harder (denser) and less compressible particles become. As particles become denser, the value of φ(β, ρ) increases, causing an increase in the primary force ($F_p$). This increase in the primary force exerted on particles results in a decrease in the time it takes the particles to reach their pressure antinodes. Accordingly, the particles can be formed so that their acoustic force response times are selected by controlling the amount of crosslinking agent incorporated into the water insoluble elastomer prior to droplet and particle formation.

The stability of elastomeric negative acoustic contrast particles can also be pre-determined based on the amount of crosslinking agent mixed into the water insoluble elastomer. To function as negative acoustic contrast particles, they must have a compressibility that allows $$\left(\frac{5\rho_p - 2\rho_o}{2\rho_p + \rho_o} < \frac{\beta_p}{\beta_o}\right),$$

but at the same time, sufficient hardness to avoid coalescing, as particles which have agglomerated into one or more large masses may be unsuitable for many applications including acoustic separation. It should be understood that creating stable elastomeric negative acoustic contrast particles that are compressible enough to function as negative acoustic contrast particles, and at the same time, hard enough to avoid coalescing is a challenging feat. Accordingly, in some embodiments it may be preferably to use a soft compressible, low molecular weight (low viscosity) dielectric silicone gel, such as PDMS or any other type of linear or cyclic low molecular weight silicone oil with crosslinking agent such as: hexamethylcyclotrisiloxane, octamethylcyclotetrasiloxane, decamethylcyclopentasiloxane, dodecamethylcyclohexasiloxane, dodecamethylpentasiloxane, and tetradecamethylhexasiloxane, as we have found that these gels can more easily be fashioned into compressible negative acoustic contrast particles that maintain stability towards coalescence, when made with 50% volume, or more, crosslinking agent.

Figure 2:
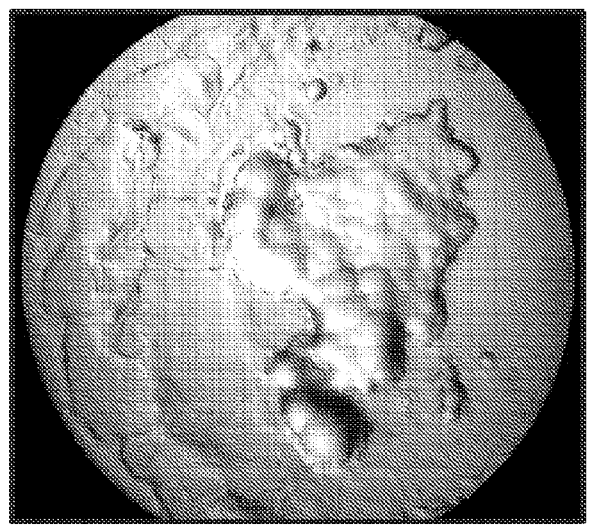
Figure 3:
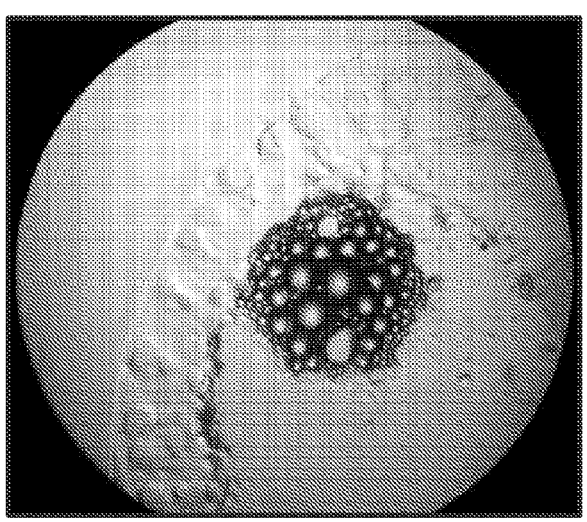
Figure 4:
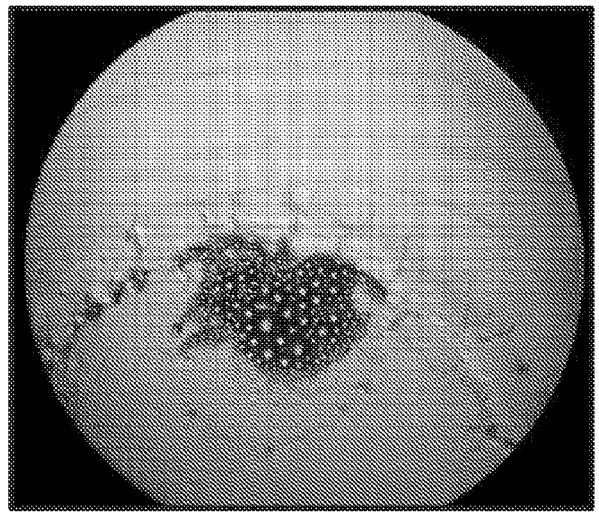

FIGS. 1-4 demonstrate the importance of using a sufficient amount of cross-linking agent in order to obtain stable elastomeric negative acoustic contrast particles that do not coalesce. FIG. 1 shows the results of emulsifying PDMS with 420 cST viscosity with 10% volume cross-linking agent. As shown, the particles coalesce and do not form stable, individual particles. FIG. 2 shows the results of emulsifying PDMS with 420 cST viscosity with 30% volume cross-linking agent. Again, stable, individual particles are not formed. However, as shown in FIGS. 3 and 4, stable individual particles are formed at 50% and 75% cross-linking agent, respectively.

Furthermore, it is important to make sure that the cross-linking time is neither too short, nor too long. A cross-linking time that is too short (for example, fewer than 1 hour for the particles shown in FIG. 5) can result in agglomeration of the droplets and prevent the formation of individual particles, while a cross-linking time that is too long (for example, greater than 48 hours for the particles shown in FIG. 5) can result in cracking and surface damage to the particles. Similar care must be taken with the temperature at which cross-linking takes place. Temperatures that are too low will prevent initiation of crosslinking, therefore preventing particle formation, while temperatures that are too high will allow extensive crosslinking to occur, resulting in damaged or surface altered particles.

Should a more monodisperse (mono-sized) population of elastomeric negative acoustic contrast particles be desired, the size distribution can be narrowed, for example by passing the particles through a filtration system. For example, Isopore™ membrane filters (or other such filters) can be used to narrow the size distribution of polydisperse elastomeric negative acoustic contrast particles. If such a filtration process does not result in sufficient narrowing of the distribution, T-Junction, flow focusing, and capillary microfluidic devices such as, for example, those described in Xu, et al., "Preparation of Highly Monodisperse Droplet in a T-Junction Microfluidic Device", AIChE Journal, vol. 52(9), pp. 3005-3010, 2006, Tan, et al., "Monodispersed Microfluidic Droplet Generation by Shear Focusing Microfluidic Device", Sensors and Actuators B: Chemical, vol. 114(1), pp. 350-356, 2006, and Weitz, et al., "Designing Emulsions Using Microfluidics", Materials Today, vol. 11 (4), pp. 18-27, 2008, can be used to produce an even more monodisperse population of elastomeric negative acoustic contrast particles.

According to one specific example, stable elastomeric negative acoustic contrast particles can be synthesized by emulsifying (e.g., by shaking or by use of a homogenizer or mixer such as the Ultra-Turaxx IKA® WERKE mixer) a 1:1 (w:w) mixture of a dielectric silicone gel (low viscosity PDMS at 420 centipoise) pre-polymer and its crosslinking agent in the presence of any amphiphillic surfactant (or mixture of two or more amphiphillic surfactants) such as, but not limited to, positively charged quarternary ammonium surfactants (e.g. 1% weight cetyltrimethylammonium bromide), negatively charged surfactants (e.g. 0.5% weight sodium dodecyl sulfate), non-ionic surfactants (e.g. 1% vol. Tween 20) and non-ionic tri-block co-polymer surfactants (e.g. 1% weight poly(ethylene glycol)-block-poly(propylene glycol)-block-poly(ethylene glycol: Pluronic F108), in aqueous solutions. Emulsion droplets can then be cured, for example by incubation at ~70° C. (e.g. hot plate or incubator) with continuous stirring (to prevent coalescence) for an extended period of time (e.g., ~12 firs), to form elastomeric negative acoustic contrast particles. Elastomeric negative acoustic contrast particles made from a dielectric silicone gel (low viscosity PDMS) and its crosslinking agent using this methodology are polydisperse in size and have an estimated size range of 1-50 μm in diameter. This methodology is versatile and robust and can be used to synthesize elastomeric negative acoustic particles from low viscosity elastomers (e.g. dielectric silicone gels), and high viscosity elastomers (e.g. Sylgard 184) with their respective crosslinking agents.

This synthesis methodology may also be important for other applications such as production of polymeric particles (e.g. ultrasound imaging agents) for ultrasound medical imaging and diagnostic purposes.

Figure 5:
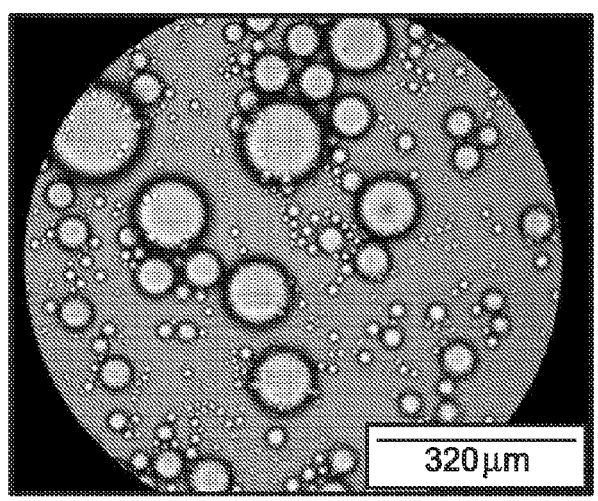
Figure 6:
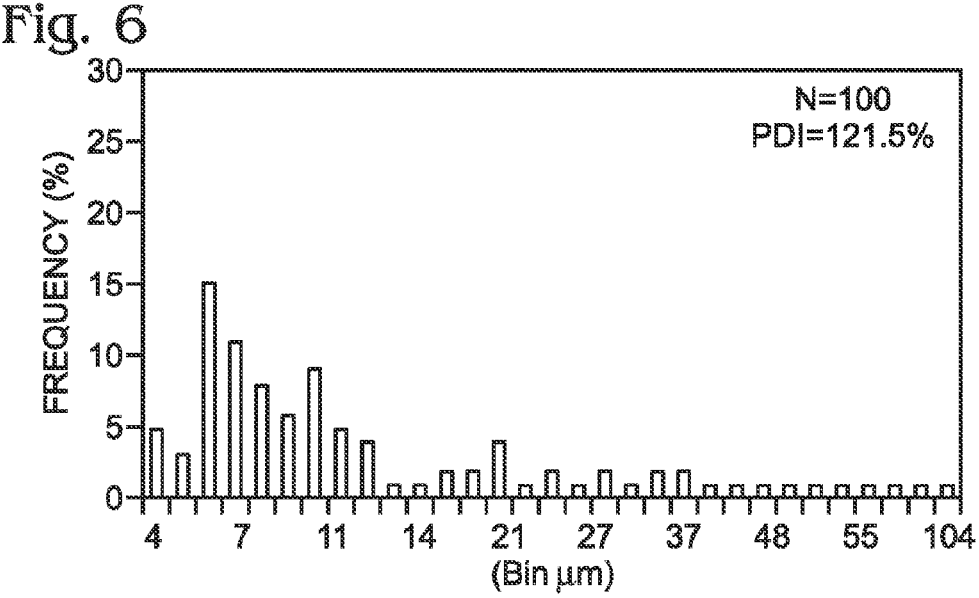
Figure 7:
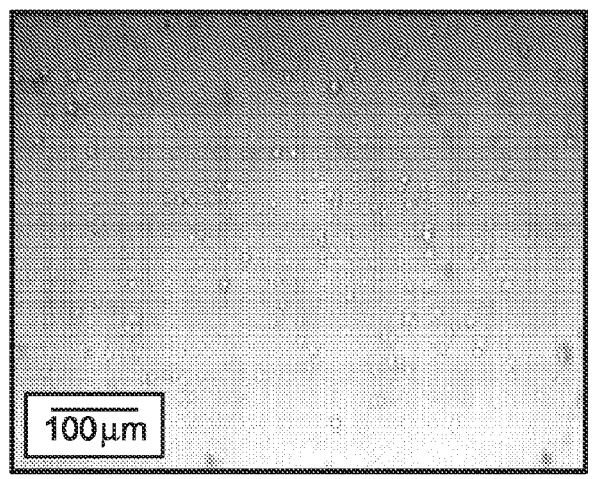

FIG. 5 shows a polydisperse population of elastomeric negative acoustic contrast particles synthesized from the dielectric silicone gel elastomer (with crosslinking agent) in an aqueous phase containing 0.5% weight sodium dodecyl sulfate (SDS) surfactant. The bar shown in FIG. 5 represents 320 μm. FIG. 6 is a size distribution histogram of the population of elastomeric negative acoustic contrast particles formed in this manner. In this population the polydispersity index (PDI), which is calculated by (standard deviation/mean)×100%=121.5%. In general, for elastomeric negative acoustic contrast particles, a population will be considered polydisperse if its PDI is greater than 10%, while a PDI below 10%, will be considered monodisperse. In FIG. 7, Isopore™ membranes (5 μm pores) were used to tighten this to an approximate size range of 1-5 μm in diameter.

As stated above, microfluidic devices can be used to emulsify low viscosity and high viscosity elastomers (with crosslinking agent) to produce monodisperse elastomeric negative acoustic contrast particles. According to some embodiments, it may be desirable to use T-junction microfluidic devices because of their ability to form droplets independently of viscosity and shear stress. According to Garstecki, P., H. A. Stone, and G. M. Whitesides, Mechanism for Flow-Rate Controlled Breakup in Confined Geometries: A Route to Monodisperse Emulsions; Phys. Rev. Lett, 94 (2005), in a T-Junction device, at low capillary number, the formation of monodisperse droplets at the junction is not due to viscous or shear forces but due to the pressure drop across the budding droplet. This property in T-Junction microfluidic devices is what makes them ideal for generating monodisperse elastomeric negative acoustic contrast particles from low and high viscosity water insoluble elastomers with their crosslinking agent.

For example, a dielectric silicone gel composed of relatively low viscosity (420 centipoise) polydimethoxysilane (PDMS) can be used to form monodisperse elastomeric negative acoustic contrast particles using T-Junction microfluidic devices. Suitable T-Junction microfluidic devices can be fabricated in PDMS, but not limited to, using standard micromolding processes such as those described in Whitesides, et al., Polydimethylsiloxane as a Material for Fabricating Microfluidic Devices; Accounts of Chemical Research, Vol. 35, No. 7 (2002).

Figure 8:
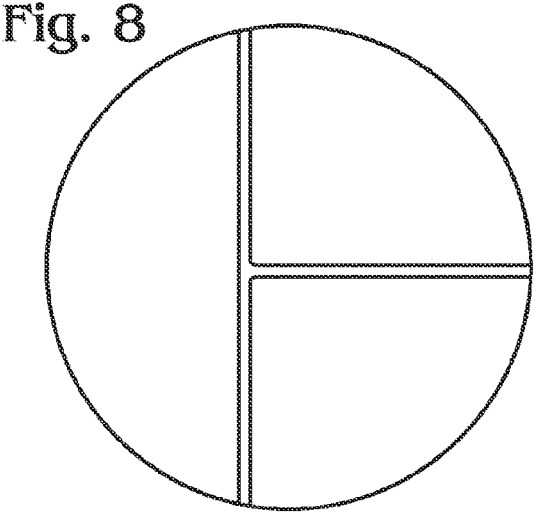
Figure 9:
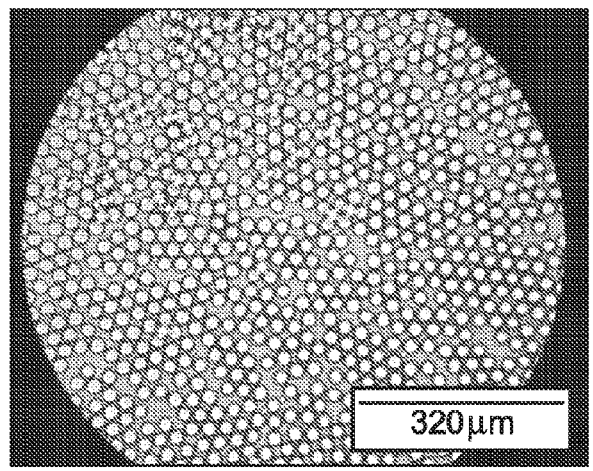
Figure 10:
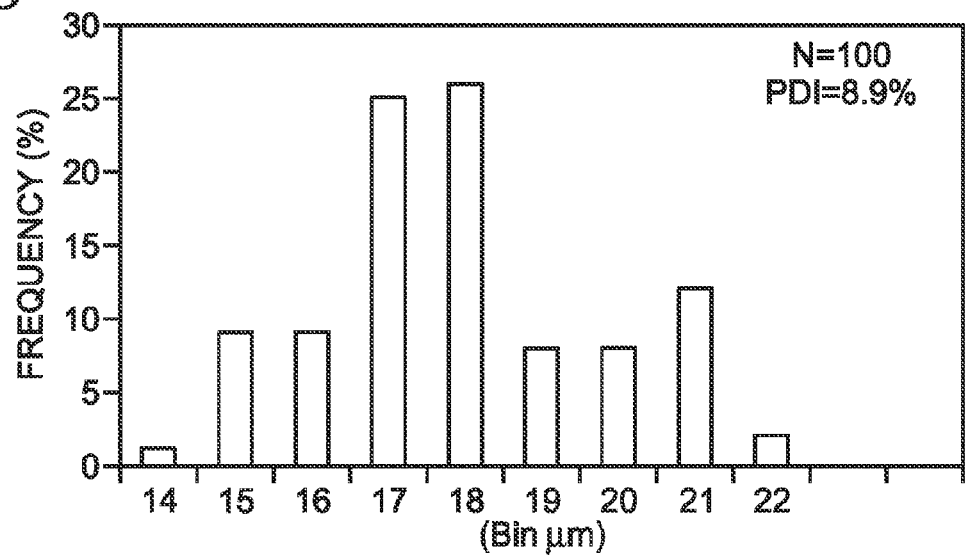
FIG. 10 is a size distribution histogram of the elastomeric negative acoustic contrast particles shown in FIG. 5.

A suitable microfluidic device is shown in FIG. 8. According to a specific embodiment, microfluidic channels having a width of 10 μm and a depth of 15 μm may be suitable. The microfluidic channels can be plasma cleaned before sealing to an oxidized glass surface. According to an embodiment, once the channels are sealed and connected to microsyringe pumps (PicoPlus: Harvard Apparatus), or other suitable apparatus, with, for example, tygon tubing (or polyethylene tubing), reagents can be pumped into the channels at specified flow rates. According to an embodiment, the dispersed phase, containing dielectric silicone gel with, for example, 50% volume crosslinking agent, is injected into the central channel at a rate of 0.08 μl/min using a microsyringe controlled by a microsyringe pump (PicoPlus: Harvard Apparatus). The continuous phase, containing 0.5% volume SDS in aqueous, is injected into the adjacent channel at a flow rate of 2 μl/min. As shown in FIGS. 9 and 10, the droplets produced with this method are relatively monodisperse with particle diameters of approximately 18 μm. In FIG. 9, the bar represents 320 μm. It will be appreciated that particle diameter can be specifically engineered, for example, by increasing or decreasing the size of the microfluidic channels at the channel junction, or by altering flow rates, surfactant concentration, crosslinking agent concentration and/or the viscosity of the phases.

Figure 11:
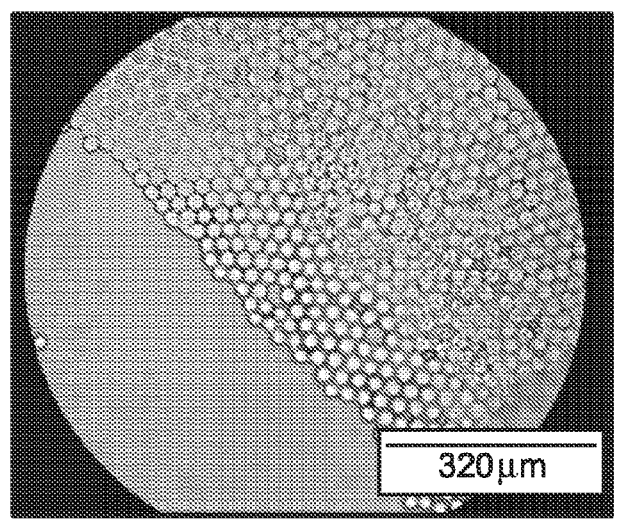
FIG. 11 is a bright field image showing the elastomeric negative acoustic contrast particles of FIG. 5 cross-linked and dried on the glass slide.

According to the histogram shown in FIG. 10, the PDI for the population of particles using this device was 8.9%, which is commensurate with commercial requirements for monodisperse bead population. These droplets can then be cross-linked (or cured) for an extended period of time (e.g., ~12 hrs in a 70° C. incubator or heating plate) to form hardened elastomeric negative acoustic contrast particles as shown in FIG. 11. According to some embodiments, mixtures of 50% or more cross-linking agent show stability (i.e. lack of coalescence) when dried on a glass slide.

Figure 12:
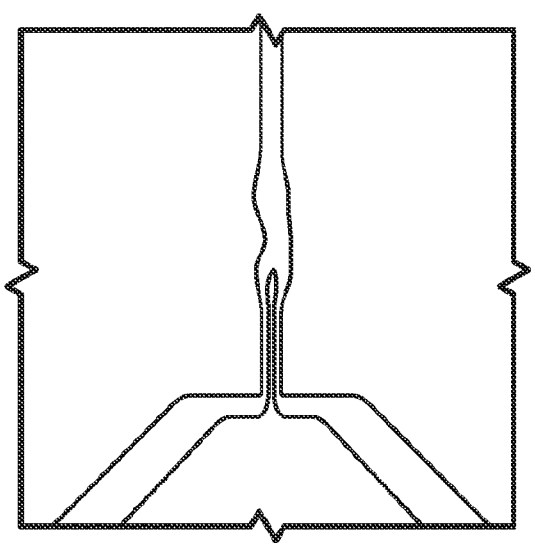
FIG. 12 is a Y-junction microfluidic device suitable for use with the methods described herein.

The microfluidic device-based method described herein can be used to synthesize monodisperse elastomeric negative acoustic contrast particles from a wide range of water insoluble elastomers (with crosslinking agent) with different viscosities (at least within the range of 1-3900 centipoise). It will be understood that the microfluidic device of FIG. 8, which shows a T-shaped junction, is not the only suitable device shape. For example a microfluidic device having a Y-shaped (flow focusing) junction, as shown in FIG. 12, may also be used. Alternatively, capillary microfluidic devices may also be used for the synthesis of monodisperse elastomeric negative acoustic contrast particles.

According to yet another embodiment, ink jet printing technologies can be used to produce monodisperse elastomeric negative acoustic contrast particles. Ink jet methods have been used to make uniformly sized biodegradable microspheres (e.g. poly-lactide-co-glycolide) loaded with medicinal drugs (e.g. Paclitaxel) (See, e.g., D. Radulescu, D. Wawro, N. Schwade. "Uniform Paclitaxel Loaded Biodegradable Microsphere Manufactured by Ink-Jet Printing" Proceedings of 11th International Symposium and Exhibition on Recent Advantages in Drug-Delivery Systems, Controlled Release Society, Salt Lake City, Utah (2003) 1-5; Y. Yeo, O. A. Basaran, K. Park. "A New Process for Making Reservoir Type Microcapsules Using Ink-Jet Technology and Interfacial Phase Separation" J. Control Release 93 (2003) 161-173; D. Radulescu, N. Schwade, D. Wawro. "Uniform Paclitaxel-Loaded Biodegradable Microsphere Manufactured by Ink-Jet Technology" Proc., Recent Adv. in Drug Delivery Sys. March (2003) 1-5; and D. Radulescu, H. J. Trost, D. T. Taylor, B. Antohe, D. Silva. "3D Printing of Biological Materials for Drug Delivery and Tissue Engineering Applications" Digital Fabrication 2005 (2005) 18-21) and high explosives (e.g. TNT) (See, e.g., R. A. Fletcher, J. A. Brazin, M. E. Staymates, B. A. Benner Jr, J. G. Gillen. "Fabrication of Polymer Microsphere Particle Standards Containing Trace Explosives Using an Oil/Water Emulsion Solvent Extraction Piezoelectric Printing Process" Talanta 76 (2008) 949-955). Ink jet printing techniques have also been used for the production of gas filled (hollow) monodisperse capsules that function as an ultrasonically activated drug delivery system. See, e.g., W. Shi, M. Bohmer, S. de Winter, J. Steenbakkers, M. Emmer, A. van Wamel, N. de Jong, C. S. Hall. "Ultrasonic Characterization of Novel Monodispersed Contrast Agents" 2006 IEEE Ultrasonics Symposium (2006) 301-304. Additionally, ink jet printing techniques have been used for the production of monodisperse polymeric particles made from poly-lactide, poly-lactide-co-glycolide, and polycaprolacton. See, e.g., M. R. Bohmer, R. Schroeders, J. Steenbakkers, S. De Winter, P. A. Duineveld, J. Lub, W. Nijssen, J. Pikkemaat, H. R. Stapert. "Preparation of Monodisperse Polymer Particles and Capsules by Ink-Jet Printing" Colloids and Surfaces A: Physicochem. Eng. Aspects 289 (2006) 96-104.

Suitable ink jet printing technologies include, but are not limited to, piezo, continuous, and thermal printers. FIG. 13 depicts an example of ink jet printing technology used to form monodisperse elastomeric negative acoustic contrast particles. As shown, droplets a water insoluble elastomer (e.g. PDMS) combined with its crosslinking agent 12 are released from an ink jet printer nozzle 14 into an aqueous phase 16 with a stabilizing surfactant such as SDS to produce monodisperse elastomeric droplets 18 that can be cured to form monodisperse elastomeric negative acoustic contrast particles.

A wide range of elastomeric negative acoustic contrast particles can be synthesized in an analogous manner including: natural rubbers, polyurethanes, silicone rubbers, butyl rubbers, polybutadienes, styrene butadienes, fluoroelastomers, polyether block amides, ethylene-vinyl acetates, and polyacrylic rubber. For certain elastomers, it may be useful to use a different type of emulsion (e.g., water in oil, oil in fluorocarbon, fluorocarbon in oil, water in fluorocarbon, fluorocarbon in water, microemulsions).

Embodiments of the present invention can include, but are not limited to, applications that use acoustic radiation, such as, ultrasound imaging, ultrasound based drug delivery, and bioseparations. Other embodiments can include, but are not limited to, applications that may not use acoustic radiation, but still require controlled elasticity and density.

As demonstrated in FIG. 14, the monodisperse elastomeric negative acoustic contrast particles of the present invention may be used as part of a powerful bioanalytical methodology. For example, biospecific elastomeric negative acoustic contrast particles 20 that have been previously mixed with a biological sample can be separated from other (positive acoustic contrast) particles 22 in the sample by using acoustic pressure radiation fields (e.g. acoustic standing, cylindrical, or spherical wave fields). The acoustic pressure radiation field (e.g. acoustic dipole excitation) can focus the positive acoustic contrast particles to their pressure potential minima (e.g. pressure nodes) while focusing the elastomeric negative acoustic contrast particles to their pressure potential minima (e.g. pressure antinodes) along the side of the focusing chamber 24. These focused positive acoustic contrast particles can then be removed from the chamber leaving only negative acoustic contrast particles. Elastomeric negative acoustic contrast particles can then be focused to the middle of the acoustic focusing chamber (e.g. acoustic axisymmetric excitation). Once the elastomeric negative acoustic contrast particles are focused to the central axis of the flow stream, they can be analyzed accurately using, for example, flow cytometry.

A comparison of FIGS. 15 and 16 shows the effects of an acoustic radiation pressure field on the elastomeric negative acoustic contrast particles of the present disclosure (FIG. 15) and positive acoustic contrast polystyrene particles (FIG. 16.) As shown, the elastomeric negative acoustic contrast particles of the present disclosure are focused to acoustic pressure field potential minima (pressure antinodes) along the side of the acoustic focusing chamber while the polystyrene particles function as positive acoustic contrast particles and are focused to the acoustic pressure potential minima along the center of the acoustic focusing chamber (pressure nodes).

Alternatively or additionally, biospecific elastomeric negative acoustic contrast particles can be trapped (i.e., immobilized) at the walls of an acoustic chamber prior to introducing an analysis mixture into the chamber. Sample can be allowed to react with the biospecific elastomeric negative acoustic contrast particles for a given time (or at a given flow rate) after which (or during which) positive acoustic contrast particles in the sample (e.g. cells) are focused to the center of the chamber (and thus separated from the biospecific elastomeric negative acoustic contrast particles) and then flowed out of the focusing chamber. An acoustic axisymmetric field could then be generated to focus the elastomeric negative acoustic contrast particles and allow for accurate analysis to occur via flow cytometry based methods.

Figure 21:
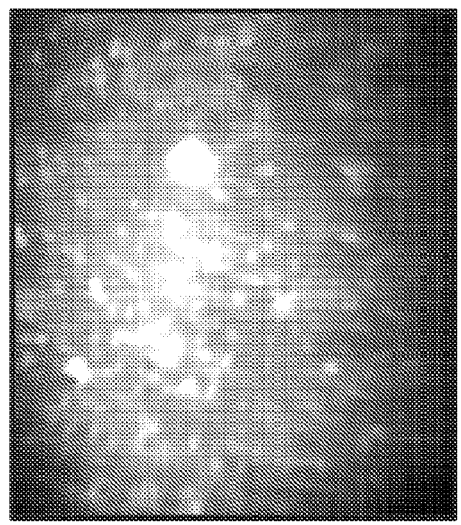
FIG. 21 shows elastomeric negative acoustic contrast particles in an acoustic chamber with the acoustic radiation field turned off.
Figure 22:
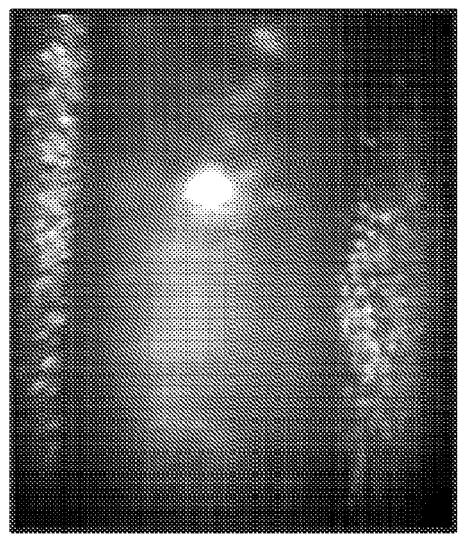
Figure 23:
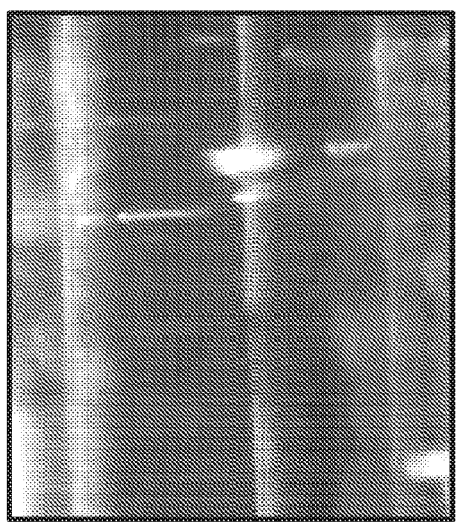
FIG. 23, shows both negative elastomeric and positive polystyrene acoustic contrast particles in a chamber.

FIG. 21 shows elastomeric negative acoustic contrast particles in an acoustic chamber with the acoustic radiation field turned off, while FIG. 22 shows the same particles with the acoustic radiation field turned on. It can be seen that the particles accumulate at the acoustic pressure antinodes along the side of the acoustic chamber. In FIG. 23, the chamber includes negative elastomeric and positive polystyrene acoustic contrast particles. As shown, when the acoustic radiation field is turned on, the polystyrene positive acoustic contrast particles are positioned at the acoustic pressure nodes in the center of the chamber, while the elastomeric negative acoustic contrast particles are positioned at the acoustic pressure antinodes along the side of the chamber.

To be used in bioassays, elastomeric negative acoustic contrast particles must have functionally stable biomolecules (e.g., antibodies, oligonucleotides, or receptors) attached to their surfaces. Stable attachment of biomolecules, along with blocking of unreacted surface areas, will allow for specific binding and subsequent quantification of targeted analytes. Because many elastomers such as PDMS have few reactive functional groups from which to anchor biological receptors and ligands, treatment of the elastomeric negative acoustic contrast particles with a basic solution should produce reactive silanol groups on their surfaces, which can further react with silane coupling agents such as aminopropyltriethoxy silane (APTES), to render an amine terminated surface. Once elastomeric negative acoustic contrast particles, with such surface chemistries are obtained, virtually any protein or nucleic acid can be covalently immobilized via well established covalent conjugation methodologies. Assemblies that incorporate biomodular coupling schemes (e.g. use of biotin/streptavidin coupling) can also be used. Once biomolecules have been attached, blocking methodologies can be incorporated using standard blocking reagents (e.g., BSA, gelatin or appropriate surfactants).

FIG. 17 shows an exemplary method of biologically functionalizing elastomeric negative acoustic contrast particles of the present disclosure to serve as platforms for bioassays. As shown, an elastomeric negative acoustic contrast particle 30 is exposed to avidin proteins 32 under sufficient conditions to allow the proteins to attach to the particle. The particle is then exposed to a biotinylated antibody 34, which bonds to the avidin protein producing functionalized particles 36.

Figure 18:
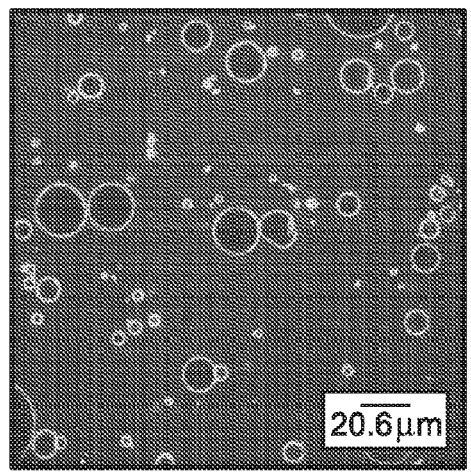
FIG. 18 shows Streptavidin-coated elastomeric negative acoustic contrast particles.
Figure 19:
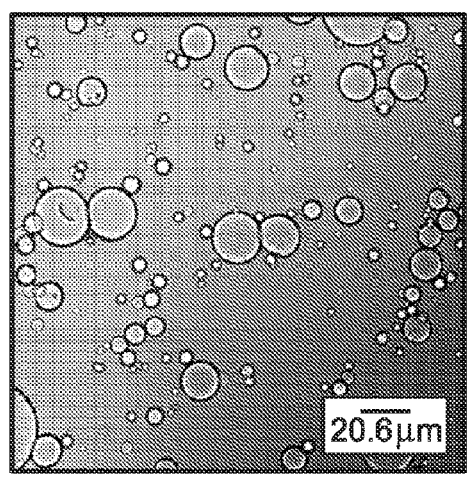
FIG. 19 is a bright field image of streptavidin-coated elastomeric negative acoustic contrast particles.
Figure 20:
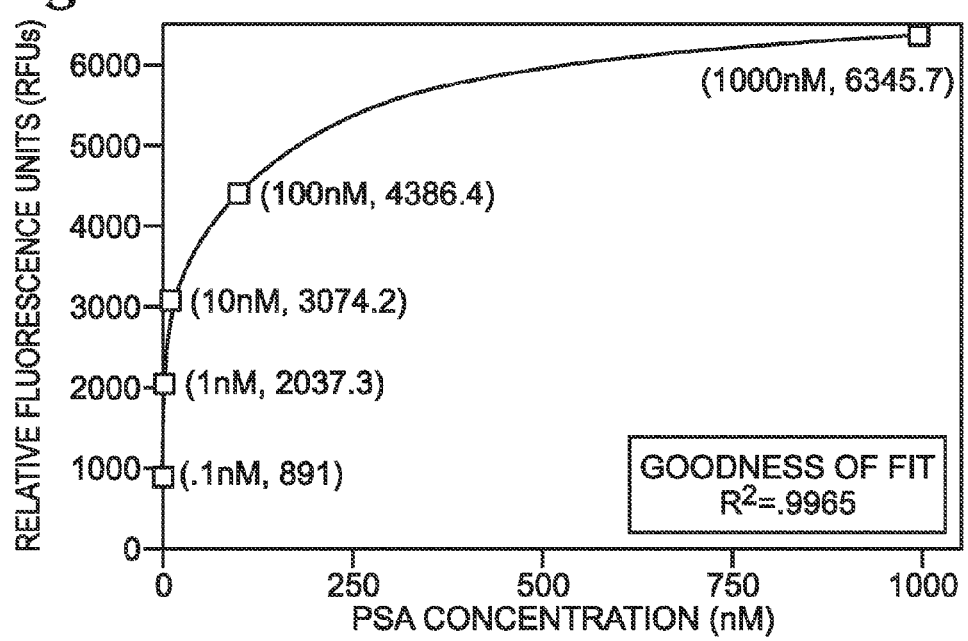
FIG. 20 shows elastomeric negative acoustic contrast particles (Sylgard 184) function as a platform for prostate specific antigen bioassay.

According to an embodiment, functionalization of elastomeric negative acoustic contrast particles for immunoassay can occur by incubating them in a 0.56 µM solution of avidin see e.g., Goldman, et al., Avidin: A Natural Bridge for Quantum Dot-Antibody Conjugates; J. Am. Chem. Soc. 124, 6378-6382 (2002) overnight, and then reacting them with a 1.7×$10^{-8}$ M solution of biotinylated monoclonal antibody and a blocking agent (e.g. 0.1% dodecyl maltoside, DDM). FIGS. 18 and 19 show elastomeric negative acoustic contrast particles that have been functionalized as described. Alternatively, 1.2 µM streptavidin-rhodamine B conjugate could be used in place of avidin. When prostate specific antigen (PSA) is used as a model analyte in this system, biofunctionalized elastomeric negative acoustic contrast particles can be reacted with PSA concentrations ranging from 0.1-1000 nM and detected using a plate reader and an Alexa 647-labeled PSA polyclonal antibody ($6.9 \times 10^{-8}$ M) as shown in FIG. 20.

These bioanalytical methods will allow elastomeric negative acoustic contrast capture particles to function in sensitive biological assays where unwanted material can be separated and removed from ligand bound elastomeric negative acoustic contrast capture particles. Removal of unwanted material from ligand bound elastomeric negative acoustic contrast capture particles will eliminate background and allow for greater sensitivity and accuracy of measurements.

As stated above, the methods described herein can be used to engineer elastomeric negative acoustic contrast particles have specific known characteristics such as density and compressibility in order to create particles having specific expected behaviors within an acoustic field. Accordingly, elastomeric acoustic contrast particles having different expected behaviors (for example positive and negative acoustic contrast) could be functionalized with different functional groups, for example, to allow for separation of multiple targets within the same sample population.

Other possible uses of elastomeric acoustic contrast particles may be found in any technological application that uses ultrasound radiation, including imaging, chemical synthesis, and ultrasound-triggered drug delivery.

It is noted that, as used in this specification and the appended claims, the singular forms "a," "an," and "the," include plural referents unless expressly and unequivocally limited to one referent. Thus, for example, reference to "a microparticle" includes two or more different microparticles. As used herein, the term "include" and its grammatical variants are intended to be non-limiting, such that recitation of items in a list is not to the exclusion of other like items that can be substituted or other items that can be added to the listed items.

Upon studying the disclosure, it will be apparent to those skilled in the art that various modifications and variations can be made in the devices and methods of various embodiments of the invention. Other embodiments will be apparent to those skilled in the art from consideration of the specification and practice of the embodiments disclosed herein. It is intended that the specification and examples be considered as examples only. The various embodiments are not necessarily mutually exclusive, as some embodiments can be combined with one or more other embodiments to form new embodiments.

What is claimed is:

1. A method for synthesizing elastomeric negative acoustic contrast microparticles comprising:
   emulsifying an elastomer pre-polymer with a crosslinking agent in the presence of an amphiphillic surfactant under sufficient conditions to produce emulsion droplets; and
   curing the emulsions droplets under sufficient conditions to form stable elastomeric negative acoustic contrast particles.

2. The method of claim 1 wherein the step of emulsifying comprises:
   introducing the elastomer pre-polymer and crosslinking agent into a first channel of a microfluidic device at a first flow rate; and
   introducing the aqueous phase with amphiphillic surfactant into a second channel of a microfluidic device at a second flow rate.

3. The method of claim 1 wherein the elastomer pre-polymer and crosslinking agent are released from an ink jet printer nozzle into an aqueous phase comprising the amphiphillic surfactant.

4. The method of claim 1 wherein the elastomer pre-polymer is a dielectric silicone gel.

5. The method of claim 4 wherein the soft compressible dielectric silicone gel is low viscosity polydimethylsiloxane.

6. The method of claim 1 wherein the elastomer is a high viscosity elastomer.

7. The method of claim 1 wherein the elastomer pre-polymer is emulsified with at least 50% volume crosslinking agent.

8. The method of claim 1 wherein the elastomer pre-polymer and crosslinking agent are provided in a 1:1 (w:w) mixture.

9. The method of claim 1 wherein the emulsion droplets are cured for at least 12 hours.

10. The method of claim 1 further comprising functionalizing the elastomeric negative acoustic contrast particles.

11. The method of claim 1 further comprising selecting the amount of crosslinking agent to be emulsified with the elastomeric precursor based on a desired behavior of the particle within an acoustic radiation field.

12. A method comprising:
   determining a specific desired behavior for an elastomeric acoustic contrast particle within an acoustic radiation field;
   selecting a weight percent of cross-linking agent to be emulsified with an elastomeric precursor based on the determined specific desired behavior;
   emulsifying an elastomer pre-polymer with the selected weight percent of the cross-linking agent in the presence of an amphiphillic surfactant under sufficient conditions to produce emulsion droplets; and
   curing the emulsions droplets under sufficient conditions to form stable elastomeric negative acoustic contrast particles.

13. The method of claim 12 wherein the desired behavior is a time-averaged drift force moving the particles to acoustic pressure antinodes.

* * * * *

UNITED STATES PATENT AND TRADEMARK OFFICE
Certificate

Patent No. 8,658,734 B2                                              Patented: February 25, 2014

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gabriel Lopez, Durham, NC (US); Nick Carroll, Albuquerque, NM (US); Kevin Cushing, Albuquerque, NM (US); Dimiter N. Petsev, Albuquerque, NM (US); and Steven W. Graves, Santa Fe, NM (US).

Signed and Sealed this Twenty-fifth Day of November 2014.

*DAVID WU*
*Supervisory Patent Examiner*
Art Unit 1762
Technology Center 1700